United States Patent
Stone et al.

(10) Patent No.: US 8,623,811 B2
(45) Date of Patent: Jan. 7, 2014

(54) ANTIMICROBIAL PEPTIDE, COMPOSITIONS, AND METHODS OF USE

(75) Inventors: Hongran F. Stone, Beijing (CN); Jacob M. Waugh, San Francisco, CA (US)

(73) Assignee: Revance Therapeutics, Inc., Newark, CA (US)

( * ) Notice: Subject to any disclaimer, the term of this patent is extended or adjusted under 35 U.S.C. 154(b) by 408 days.

(21) Appl. No.: 12/669,705

(22) PCT Filed: Jul. 28, 2008

(86) PCT No.: PCT/US2008/071350
§ 371 (c)(1),
(2), (4) Date: Feb. 3, 2010

(87) PCT Pub. No.: WO2009/015385
PCT Pub. Date: Jan. 29, 2009

(65) Prior Publication Data
US 2010/0215591 A1    Aug. 26, 2010

Related U.S. Application Data

(60) Provisional application No. 60/952,059, filed on Jul. 26, 2007.

(51) Int. Cl.
*A61K 38/00* (2006.01)
*A61K 38/16* (2006.01)

(52) U.S. Cl.
USPC .......................................... 514/1.1; 514/21.3

(58) Field of Classification Search
None
See application file for complete search history.

(56) References Cited

U.S. PATENT DOCUMENTS

| | | | |
|---|---|---|---|
| 5,744,166 A | 4/1998 | Illum | |
| 5,747,641 A | 5/1998 | Frankel et al. | |
| 5,804,604 A | 9/1998 | Frankel et al. | |
| 5,989,545 A | 11/1999 | Foster et al. | |
| 6,043,218 A | 3/2000 | Dix | |
| 6,296,845 B1 | 10/2001 | Sampson-Johannes et al. | |
| 6,544,548 B1 | 4/2003 | Siller-Jackson et al. | |
| 6,645,501 B2 | 11/2003 | Dowdy | |
| 6,696,038 B1 | 2/2004 | Mahato et al. | |
| 6,844,324 B1 | 1/2005 | Zhang et al. | |
| 7,008,924 B1 | 3/2006 | Yan et al. | |
| 7,056,656 B1 | 6/2006 | Rana et al. | |
| 7,060,498 B1 | 6/2006 | Wang | |
| 8,092,788 B2 | 1/2012 | Dake et al. | |
| 2002/0127247 A1 | 9/2002 | Steward et al. | |
| 2003/0118598 A1 | 6/2003 | Hunt et al. | |
| 2003/0147921 A1 | 8/2003 | Goodnough et al. | |
| 2003/0185788 A1 | 10/2003 | Rothbard et al. | |
| 2003/0215395 A1 | 11/2003 | Yu et al. | |
| 2003/0215412 A1 | 11/2003 | Waugh | |
| 2003/0229034 A1 | 12/2003 | Waugh et al. | |
| 2003/0236214 A1 | 12/2003 | Wolff et al. | |
| 2004/0019181 A1 | 1/2004 | Falla et al. | |
| 2004/0220100 A1 | 11/2004 | Waugh et al. | |
| 2004/0229801 A1* | 11/2004 | Kawabe et al. | 514/12 |
| 2004/0247614 A1 | 12/2004 | Dorr et al. | |
| 2005/0196414 A1 | 9/2005 | Dake et al. | |
| 2005/0239705 A1 | 10/2005 | Dake et al. | |
| 2006/0115480 A1 | 6/2006 | Hillman et al. | |
| 2007/0244044 A1 | 10/2007 | O'Neil | |
| 2008/0200373 A1 | 8/2008 | Waugh et al. | |
| 2010/0168023 A1 | 7/2010 | Ruegg et al. | |

FOREIGN PATENT DOCUMENTS

| | | |
|---|---|---|
| EP | 1421948 | 5/2004 |
| EP | 1 661 912 | 5/2006 |
| RU | 2207844 C2 | 7/2003 |
| WO | WO 93/21941 | 11/1993 |
| WO | WO 94/04686 | 3/1994 |
| WO | WO 95/11038 | 4/1995 |
| WO | WO 96/11712 | 4/1996 |
| WO | WO 98/19710 | 5/1998 |
| WO | WO 00/24419 | 5/2000 |
| WO | WO 00/34308 | 6/2000 |
| WO | WO 02/07773 | 1/2002 |

(Continued)

OTHER PUBLICATIONS

Agbottah et al., "Inhibition of HIV-1 Virus Replication Using Small Soluble Tat Peptides," Virology, 345(2), pp. 373-389, 2006.

(Continued)

*Primary Examiner* — Christina Bradley
*Assistant Examiner* — Lianko Garyu
(74) *Attorney, Agent, or Firm* — Kenneth H. Sonnenfeld; Joseph D. Eng, Jr.; King & Spalding LLP

(57) ABSTRACT

The present invention provides antimicrobial peptides that exhibit a broad range of antimicrobial activity to gram positive and gram negative bacteria, as well as fungi, mold, and virus. The antimicrobial peptide of the invention is a cationic peptide, and may contain an HIV-TAT or reverse HIV-TAT sequence, or derivative thereof. The present invention further provides antimicrobial compositions containing the cationic peptide. Such compositions are especially useful for topical application to the skin, hair, nail, vagina, urethra, ear, oral cavity, nasal passage, respiratory system, opthalmic region, and various mucosal regions. The compositions of the present invention improve the condition and/or appearance of the treated region, and are suited for long-term and/or routine use to, for example, prevent or prevent the recurrence of microbial infection. The present invention further provides kits for use in improving the condition or appearance of skin, nail, or treated area. These kits may facilitate ease of use, long-term storage, and/or efficacy of the compositions.

55 Claims, No Drawings

(56) References Cited

FOREIGN PATENT DOCUMENTS

| WO | WO 02/065986 | 8/2002 |
| --- | --- | --- |
| WO | WO 02/067917 | 9/2002 |
| WO | WO 03/072049 | 9/2003 |
| WO | WO 2004/006954 | 1/2004 |
| WO | WO 2005/084361 | 9/2005 |
| WO | WO 2005/084410 | 9/2005 |
| WO | WO 2005/120546 | 12/2005 |
| WO | WO 2006/050611 | 5/2006 |
| WO | WO 2006/094193 | 9/2006 |
| WO | WO 2006/094263 | 9/2006 |
| WO | WO 2006/105450 | 10/2006 |
| WO | WO 2007/059528 | 11/2007 |
| WO | WO 2008/082885 | 7/2008 |
| WO | WO 2008/082889 | 7/2008 |
| WO | WO 2010/078242 | 7/2010 |

OTHER PUBLICATIONS

Henriques. et al., "Cell Penetrating Peptides and Antimicrobial Peptides: How Different Are they?" Biochem. J., 399, pp. 1-7, 2006.
Jung et al., "Biological Activity of Tat (47-58) Peptide on Human Pathogenic Fungi," Biochemical and Biophysical Research Communications, 345, pp. 222-228, 2006.
Jung et al., "Effective Antibacterial Action of Tat (47-58) by Increased Uptake into Bacterial Cells in the Presence of Trypsin," J. Microbiol. Biotechnol., 18(5), pp. 990-996, 2008.
1992 Sigma Catalog, pp. 1745.
Console et al., "Antennapedia and HIV Transactivator of Transcription (TAT) "Protein Transduction Domains" Promote Endocytosis of High Molecular Weight Cargo Upon Binding to Cell Surface Glycosaminoglycans", J. of Biological Chemistry, vol. 278, No. 37, Sep. 2003, pp. 35109-35114.
Fawell et al., "TAT-Mediated Delivery of Heterologous Proteins into Cells," Proc. Natl. Acad. Sci. vol. 91, pp. 664-668, 1994.
Futaki, "Intracellular Delivery of Biopolymers Using Membrane-Permeable Peptides," Membrane, 28(2), pp. 55-60, 2003.
Green, M. "Mutational analysis of HIV-1 TAT minimal domain peptides: identification of trans-dominant mutants that suppress HIV-LTR-driven gene expression", Cell, 58:215-223, 1989.
Kalderon et al., "A Short Amino Acid Sequence Abie to Specify Nuclear Location," Cell, vol. 39, pp. 499-509, 1984.
Nagahara et al., "Transduction of Full-Length TAT Fusion Proteins into mammalian Cells: TAT-p27$^{kip1}$ Induces Cell Migration," Nature Medicine, vol. 1, No. 12, pp. 1449-1452, 1998.
Park et al., "Mutational Analysis of a Human Immunodeficiency Virus Type 1 TAT Protein Transduction Domain Which is Required for Delivery of a Exogenous Protein into Mammalian Cells," Journal of General Virology, 83, pp. 1173-1181, 2002.
Pharmalicensing, Ltd., "AIDS, Use of HIV-1 TAT, To Target and/or Activate Antigen-Presenting Cells, and/or to Deliver Cargo Molecules," from http://pharmalicensing.com/public/outlicensing/view/3766, 2001, 3 pages.
Schwartz et al., Peptide-Mediated Cellular Delivery Delivery, Curr. Opin. Mol. ther., vol./Iss: 2(2), pp. 162-167, 2000.
Umezawa et al., "Development of β-peptides Having Ability to Penetrate Cell Membrane." 24[P1]I-133, Faculty of Pharmaceutical Sciences, Nagoya City University, 123(2), p. 29, Mar. 2003.
Vivés et al., "A Truncated HIV-1 Tat Protein Basic Domain Rapidly Transiocates Through The Plasma Membrane And Accumulates In The Cell Nucleus," J. Biol. Chem., 272(25), pp. 16010-16017, Jun. 1997.
Voet et al., Biochemistry, 2d ed., John Wiley and Sons, Inc., pp. 1275-1276, 1995.
Wender et al., "The Design, Synthesis, and Evaluation of Molecules that Enable or Enhance Cellular Uptake: Peptoid Molecular Transporters," PNAS, 97(24), pp. 13003-13008, Nov. 21, 2000.
Zhao et al., "Intracellular Cargo Delivery Using Tat Peptide and Derivatives," Medicinal Research Reviews, 24(1). pp. 1-12, 2004.
Revance Therapeutics, Inc., Final Office Action for U.S. Appl. No. 12/897,188 dated Mar. 25, 2013, 17 pages.

* cited by examiner

ANTIMICROBIAL PEPTIDE, COMPOSITIONS, AND METHODS OF USE

This Application claims priority to U.S. Provisional Application No. 60/952,059 filed Jul. 26, 2007, which is hereby incorporated by reference in its entirety.

FIELD OF THE INVENTION

The invention relates to antimicrobial peptides for use in pharmaceutical and cosmetic applications, to treat or prevent microbial infections, and/or prevent the recurrence of a microbial infection after treatment.

BACKGROUND OF THE INVENTION

Small, cationic antimicrobial peptides (AMPs) are naturally occurring antibiotics of the innate immune system. AMPs are widely distributed in animals and plants and are among the most ancient host defense factors. Their spectrum of activity may include Gram-positive and Gram-negative bacteria as well as fungi and certain viruses. As resistance of pathogenic microbes to conventional antibiotics increases, these endogenous antibiotics are an important source for designing new therapies against a variety of infectious diseases, including therapies for chronic microbial infections as well as for routine and/or prophylactic use. However, for many applications, such peptides must be, in addition to effective, sufficiently safe and stable so as to allow long term and/or routine use without negatively impacting the affected area.

SUMMARY OF THE INVENTION

The present invention provides antimicrobial peptides that exhibit a broad range of antimicrobial activity against gram positive and gram negative bacteria, as well as fungi, mold, and certain viruses. The peptides of the invention are cationic, containing positively charged amino acids such as lysine, arginine, and histidine, along with other non-charged amino acids such as glycine or glutamine. The peptides of the invention are safe, effective, and sufficiently stable to allow long-term or routine use.

The present invention further provides antimicrobial compositions containing the antimicrobial peptide. The compositions are stable, and thus may be formulated in a variety of forms including for routine use. Such compositions are especially useful for topical application to the skin, hair, nail, vagina, urethra, ear, oral cavity, nasal passage, respiratory system, opthalmic region, various mucosal regions, and other affected areas, to treat, prevent, or prevent the reoccurrence of, a microbial infection. The compositions of the present invention, by reducing, inhibiting, or preventing microbial infection, improve the condition and/or appearance of the treated region, even with long term or routine use.

The present invention further provides kits for use in improving the condition or appearance of skin, nail, or other treated area. These kits may contain components that facilitate dispensing and applying the compositions of the invention, and may be designed for convenient application and long-term storage of the compositions.

DETAILED DESCRIPTION OF THE INVENTION

Peptide fragments of HIV-TAT were used in conjunction with botulinum toxin to produce more stable, more effective, and safer botulinum toxin compositions for therapeutic, aethetic, and/or cosmetic purposes. These botulinum toxin containing compositions are disclosed in a U.S. Provisional Application filed Dec. 29, 2006, entitled "Compositions and Methods of Topical Application And Transdermal Delivery of Botulinum Toxins Stabilized With Polypeptide Fragments Derived From HIV-TAT," which is hereby incorporated by reference in its entirety. The present inventors discovered that peptide fragments of HIV-TAT, and related peptides, have antimicrobial activity, and are useful as active ingredients in pharmaceutical and cosmetic compositions. Such peptides are safe and effective for long term or routine use (e.g., in the absence of botulinum toxin).

Thus, one aspect of the present invention is a cationic peptide that comprises an HIV-TAT sequence or reverse HIV-TAT sequence at the N- or C-terminus, or both the N-terminus and the C-terminus. For example, the antimicrobial peptide may have an HIV-TAT sequence, such as Arg-Lys-Lys-Arg-Arg-Gln-Arg-Arg-Arg (SEQ ID NO:1), or reverse HIV TAT sequence, such as Arg-Arg-Arg-Gln-Arg-Arg-Lys-Lys-Arg (SEQ ID NO:2), at the N- or C-terminus or both the N-terminus and the C-terminus.

In one embodiment, the cationic peptide comprises an N-terminal portion that is an HIV-TAT or reverse HIV-TAT sequence, a C-terminal portion that is an HIV-TAT or reverse HIV-TAT sequence, and one or more cationic residues (e.g., Lys or Arg) between the N-terminal portion and the C-terminal portion. For example, the peptide may have from 5 to 20 cationic residues such as Lys between the N-terminal portion and the C-terminal portion, such as about 12, about 15, or about 17 cationic residues.

In an exemplary embodiment, the invention is a cationic peptide having the following sequence: Arg-Lys-Lys-Arg-Arg-Gln-Arg-Arg-Arg-Gly-(Lys)n-Gly-Arg-Lys-Lys-Arg-Arg-Gln-Arg-Arg-Arg (SEQ ID NO:3), or Arg-Arg-Arg-Gln-Arg-Arg-Lys-Lys-Arg-Gly-(Lys)n-Gly-Arg-Arg-Arg-Gln-Arg-Arg-Lys-Lys-Arg (SEQ ID NO:4), where n is from about 5 to about 20, such as from about 10 to about 20.

In one embodiment of the invention, the N-terminal portion of the peptide is an HIV-TAT sequence and the C-terminal portion of the peptide is an HIV-TAT sequence. In another embodiment, the N-terminal portion is a reverse HIV-TAT sequence and the C-terminal portion is a reverse HIV-TAT sequence. For example, the antimicrobial peptide may have the following amino acid sequence: Arg-Lys-Lys-Arg-Arg-Gln-Arg-Arg-Arg-Gly-(Lys)$_{15}$-Gly-Arg-Lys-Lys-Arg-Arg-Gln-Arg-Arg-Arg (SEQ ID NO:5).

In certain embodiments, the peptide contains a naturally occurring sequence of amino acids, such as an HIV-TAT sequence, but may alternatively contain improvements of the naturally occurring sequence to improve its potency. Antimicrobial peptides with improved potency may be identified using an assay as described or exemplified herein. In certain embodiments, the peptide of the invention is readily biodegradable.

Generally, antimicrobial derivatives of the HIV-TAT and reverse HIV-TAT sequence, which are contemplated by the instant invention, are characterized as having a particularly high content of Arg and Lys residues. For example, the peptide of the invention may contain at least about 50%, collectively, of Arg and Lys amino acid residues, but may contain at least about 75%, or at least about 80%, Arg and Lys residues. In these or other embodiments, such derivatives may have the amino acid sequence of SEQ ID NO: 3 or 4, with from 1 to 5 amino acid substitutions, insertions, or deletions (collectively), including 1, 2, 3, or 4 amino acid substitutions, insertions, or deletions with respect to SEQ ID NO: 3 or 4. In certain embodiments, such substitutions, insertions, or deletions, are located within the HIV-TAT or reverse HIV-TAT sequence.

The antimicrobial peptides of the invention have a length of from about 15 amino acids to about 100 amino acids. In certain embodiments, the cationic peptide is from about 25 to about 50, or from about 25 to about 40 amino acids in length. In an exemplary embodiment of the invention, the antimicrobial peptide is about 35 amino acids in length.

The present invention is effective for inhibiting, killing, and/or lysing various microbial organisms, and may have a broad antimicrobial spectrum. Exemplary bacteria for which the invention may be bacteriostatic or bactericidal include both gram-negative and gram-positive bacteria such as: *Staphylococcus aureus, Streptococcus pyogenes* (group A), *Streptococcus* spp. (viridans group), *Streptococcus agalactiae* (group B), *Streptococcus bovis, Streptococcus* (anaerobic species), *Streptococcus pneumoniae, Streptococcus mutans, Enterococcus* spp., *Neisseria gonorrhoeae, Neisseria meningitidis, Branhamella catarrhalis, Bacillus anthracis, Bacillus subtilis, Propionibacterium acnes, Corynebacterium diphtheriae, Listeria monocytogenes, Clostridium tetani, Clostridium difficile, Escherichia coli, Enterobacter* spp., *Proteus mirablis, Pseudomonas aeruginosa, Klebsiella pneumoniae, Salmonella* spp., *Shigella* spp., *Campylobacter jejuni, Actinobacillus actinomycetumcomitans, Porphyromonas gingivalis, Bacteriodes forcythus, Treponema denticola, Prevotella intermedia*, and *Eubacterium nodatum*.

Thus, the antimicrobial peptide of the invention may be useful for inhibiting such bacteria to ameliorate microbial infection(s), or reduce the likelihood of microbial infection(s), including: bacteremia, pneumonia, meningitis, osteomyelitis, endocarditis, dental caries, periodontal disease, sinusitis, rhinitis, pink eye, urinary tract infections, tetanus, gangrene, colitis, acute gastroenteritis, impetigo, acne, acne posacue, wound infections, burn infections, fascitis, bronchitis, and a variety of abscesses, nosocomial infections, and opportunistic infections.

The antimicrobial peptide of the invention is also effective for inhibiting the growth and survival of fungal organisms such as dermatophytes (e.g., *Microsporium* spp. such as *Microsporum canis, Microsporum audouinii,* and *Microsporum gypseum*; and *Trichophyton* spp., such as *T. rubrum, T. mentagrophytes, T. Trichophyton, T. schoenleinii*, and *T. tonsurans*), *Acremonium* spp., *Fusarium oxysporum, Scopulariopsis brevicaulis, Onychocola canadensis, Scytalidium dimidiatum*; yeasts (e.g., *Candida albicans, C. Tropicalis*, or other *Candida* species, and *Saccharomyces cerevisiae*), *Torulopsis glabrata, Epidermophyton floccosum, Malassezia furfur, Pityropsporon orbiculare* or ovale, *Cryptococcus neoformans, Aspergillus fumigatus, Aspergillus nidulans, Aspergillus niger* and other *Aspergillus* spp., *Zygomycetes* (e.g., *Rhizopus* and *Mucor*), *Paracoccidioides brasiliensis, Blastomyces dermatitides, Histoplasma capsulatum, Coccidioides immitis*, and *Sporothrix schenckii*.

The antimicrobial peptide is therefore useful for inhibiting fungal organisms to treat or prevent infections such as: Aspergillosis, Blastomycosis, Candidiasis, Coccidioidomycosis, Cryptococcosis, Histoplasmosis, Paracoccidiomycosis, Sporotrichosis, Zygomycosis. In certain embodiments of the invention, the antimicrobial peptide is effective for treating or preventing Tinea pedis, Tinea versicolor, and Onychomycosis. Other fungal infections for which the antimicrobial peptide of the invention is effective, include: Tinea barbae, Lobomycosis, Mycetoma, Piedra, Pityriasis versicolor, Tinea capitis, Tinea corporis, Tinea cruris, Tinea favosa, Tinea nigra, Otomycosis, Phaeohyphomycosis, and Rhinosporidiosis.

The present invention is also effective against certain viruses, such as HIV, herpes simplex viruses, cytomegalovirus, and human papillomavirus. Thus, the antimicrobial peptide of the invention is also effective for preventing and treating infections such as cold sores, genital herpes, and warts, and effective for preventing HIV infection.

The present invention provides a pharmaceutical or cosmetic composition containing the antimicrobial peptide of the invention, and a pharmaceutically or cosmetically acceptable carrier and/or diluent. Generally, the compositions of the invention do not contain botulinum toxin, as disclosed in the U.S. Provisional Application filed Dec. 29, 2006, entitled "Compositions and Methods of Topical Application And Transdermal Delivery of Botulinum Toxins Stabilized With Polypeptide Fragments Derived From HIV-TAT," and that is incorporated by reference herein.

The compositions of the invention may comprise, consist of, or consist essentially of, the antimicrobial peptide of the invention in an amount effective for antimicrobial activity, in combination with a carrier and/or diluent. In this respect, the term "consists essentially of" means that the composition contains only the antimicrobial peptide with pharmaceutically or cosmetically acceptable carrier(s) and/or diluent(s), and may optionally contain an additional antimicrobial agent(s), such as an antibiotic, or an anti-inflammatory agent (e.g., NSAID). For example, when formulated for topical administration, the composition of the invention may optionally contain Benzoyl peroxide, Clindamycin, Erythromycin, Tetracycline, Bacitracin, Neomycin, Mupirocin, Polymyxin B, Miconazole, and/or Clotrimazole. In certain embodiments, the carrier and/or diluent is an aqueous carrier or diluent, such as buffered saline.

The pharmaceutical or cosmetic composition of the invention may be formulated for topical administration, which can be a welcome alternative to systemic therapy for treating or preventing many microbial infections. In certain embodiments, topical therapy with the composition of the invention is administered alongside a systemic or other topical therapy to provide either additive or synergistic results. For example, the antimicrobial peptide of the invention may act synergistically with one or more of Benzoyl peroxide, Clindamycin, Erythromycin, Tetracycline, Bacitracin, Neomycin, Mupirocin, Polymyxin B, Miconazole, Clotrimazole and/or equivalent antimicrobial agents.

Treatment with the composition of the invention may not only clear various microbial infections, but is also effective for preventing the occurrence of such infections in a first instance, and for preventing recurrence of such infections. In this latter aspect, the present composition is administered to the affected region after treatment with topical or systemic therapy. To prevent recurrence of an effectively treated infection, or to prevent occurrence of an infection in a first instance at a susceptible region, the composition may be administered routinely (e.g., daily) for a long period of time, including for days, weeks, or even years.

When formulated for topical administration, the composition of the present invention may contain ingredients typical in topical pharmaceutical or cosmetic compositions, such as a carrier, vehicle or medium. Specifically, the carrier, vehicle, or medium is compatible with the tissues to which it will be applied, such as the skin, hair, nail, vagina, urethra, ear, oral cavity, nasal passage, respiratory system, opthalmic region, and/or mucosa. The compositions and components of the invention are suitable for contacting infected tissues or for use in patients in general without undue toxicity, incompatibility, instability, allergic response, and the like. As appropriate, compositions of the invention may comprise any ingredient conventionally used in the fields under consideration.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain: additional antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals. In certain embodiments, the composition of the invention is formulated with the above ingredients so as to be stable for a long period of time, as may be beneficial where continual or long-term treatment is intended.

The compositions of the invention may be in the form of controlled-release or sustained-release compositions, wherein the antimicrobial peptide along with additional active agents are encapsulated or otherwise contained within a material, such that they are released onto the skin or affected area in a controlled manner over time. The compositions of the invention may be contained within or on matrixes, liposomes, vesicles, microcapsules, microspheres and the like, or within or on a solid particulate material.

Administration of the composition of the invention may be to any affected or susceptible region, for example, to the legs, shoulders, back (including lower back), axilla, palms, feet, neck, groin, dorsa or the hands or feet, elbows, upper arms, knees, upper legs, buttocks, torso, pelvis, or any other part of the body for which treatment or prevention of infection may be desired. Such treatment is also contemplated for treating and/or dressing wounds, such as cuts, scrapes, and burns to the skin, so as to treat or prevent infection of the wounded area.

The compositions of the invention are suitable for use in physiologic environments with a pH ranging from about 4.5 to about 6.3, and thus, the compositions may be formulated at a similar or equivalent pH. The compositions according to this invention may be stored either at room temperature or under refrigerated conditions.

The composition of the invention contains an amount of antimicrobial peptide effective for antimicrobial action. Generally, the composition contains from about 0.01% (wt./vol.) to about 20% antimicrobial peptide. In certain embodiments, the composition contains from about 0.5% to about 10% antimicrobial peptide, such as about 0.5%, about 1%, about 5%, or about 10% antimicrobial peptide.

In one embodiment, the pharmaceutical composition of the invention is a cleanser or moisturizer. Cleansers and moisturizers of the invention may be particularly useful for conditioning the skin while treating and/or preventing a microbial infection, such as acne including propionicbacterium acne. This aspect of the invention is also effective for preventing the reoccurrence of acne after the acne has effectively dissipated. In this aspect, the cleanser or moisturizer may be applied to the effected area routinely, e.g., approximately daily, and on a continual or routine basis. For example, treatment may be continual for days, weeks, months, or even years.

In another embodiment, the composition of the invention is a topical solution effective against Athlete's feet (Tinea pedis), and/or onychomycosis. In this aspect, the composition may be an aqueous solution for soaking or painting the affected region. In this embodiment, the invention is also effective for preventing the recurrence of the condition, by continual daily treatment. Further, when used for the treatment of onychomycosis, the composition of the invention may be used alongside systemic therapy, such as, for example, Lamisil®, to provide more effective results and to improve the condition and/or appearance of the nails.

In other embodiments, the composition of the invention is formulated as a mouth wash, oral spray, or oral gel. In this aspect, the mouthwash or oral spray of the invention is effective for the prevention of dental caries, for the treatment and/or prevention of periodontal disease, for the treatment of sore throat, or to treat or prevent halitosis that might be caused by the presence or activity of microbes. When formulated as an oral gel, the composition of the invention is effective for the treatment and prevention of sores around the mouth, such as cold sores and canker sores. When formulated as a mouthwash, oral spray, or oral gel, the composition generally contains from about 0.01% to about 10% of the antimicrobial peptide, such as about 1%, about 2%, about 3%, or about 5% antimicrobial peptide.

In yet another embodiment, the invention is formulated as a cream or lotion. Such formulations are particularly suitable for the treatment and/or prevention of herpes simplex virus infection or outbreak. Thus, in certain embodiments, the invention is suitable for treatment genital herpes, cold sores, or chicken pox.

The composition of the invention may also be formulated as a nasal spray effective against rhinitis, or formulated as an eye drop effective against pink eye.

In another aspect, the invention provides a method for treating or preventing a condition associated with a microbial infection. The method of the invention comprises administering the pharmaceutical or cosmetic composition of the invention, containing the antimicrobial peptide, to a patient having or suspected of having a microbial infection. In certain embodiments, the composition is administered to the patient after treatment of the infection, either with the composition of the invention or with an alternative therapy, to prevent further recurrence. The patient may be any veterinary or human patient.

The compositions of the invention are useful for the treatment and/or prevention of local and systemic bacterial, fungal, and viral infection to the skin, the hair, the nail, the vagina, the urethra, the ear, the oral cavity, the respiratory system, the opthalmic region, the nasal, and various mucosal regions via topical route or systemic infection by various routes, such as intravenously or subdermally. Such diseases can be, for example, acne including propionicbacterium acne, onychomycosis, athelete's feet, genital herpes, caries, peridontal disease, rhinitis, and pink eye. In exemplary embodiments, the infection is an infection of *Staphylococcus aureus, Pseudomonas aeruginosa, Escherichia coli, Candida albicans, Aspergillus niger*, and/or a herpes simplex virus.

In order to treat, prevent, or prevent recurrence of, microbial infection, the antimicrobial peptide may be administered at least once a day for at least about one week. Alternatively, the composition is administered at least twice a day for at least two days. In certain embodiments, the composition is administered approximately daily, at least daily, twice a week, weekly, or for about one month. In certain embodiments, the composition of the invention is administered for several months, such as at least two months, six months, or about one year or longer. The invention is further suited for long-term use, which may be particularly beneficial for preventing recurring infection, or for preventing infection or conditions in at-risk or susceptible patients, including immune compromised patients. Such long-term use may involve treatment for at least two years, three years, four years, or even five or more years.

In another aspect, the composition of the invention is a kit, which contains the peptide or compositions of the invention packaged to facilitate dispensing and/or applying the composition to affected or susceptible regions. The packaging or dispenser may include a bottle, tube, spray bottle, or other dispenser. In certain embodiments of the invention, the composition is packaged in a concentrated form, and diluted to a desired concentration upon use by the end user. In this or other aspect, the composition is formulated and packaged in a manner suitable for long-term storage to maintain efficacy of the composition.

The kit may further include additional components to facilitate application of the composition to the affected area, such as, for example, a brush, sponge, cotton swab, or the like.

EXAMPLES

Example 1

Effect of Peptide on Conditions Characterized by Microbial Infection

The following experiments are designed to test the effects of a diluent formulation; however, surprisingly, it is found that the cationic peptide is itself a potent antimicrobial. It is discovered that the peptide of the invention is not only safe for long-term use, but effective for treating and preventing, including preventing recurrence of, various conditions associated with microbial infection. The effect of the peptide on microbial growth was tested in Example 2.

Example 1.1

A 15-year-old male with a two-year history of acne uses topical 5% peptide (SEQ ID NO:5) formulation twice a day for 4 weeks. The cream formulation is composed of the excipients cetyl alcohol, isopropyl myristate, stearyl alcohol, butylated hydroxytolune, polyoxyethylene stearyl ether, polyoxyethylene stearyl ether, edetate disodium, and purified water. The acne disappears in two weeks with use of the topical formulation. With continued use of the formulation for two years, no new breakouts or adverse events are observed.

Example 1.2

A 36 year-old female who has Tinea Pedis (Athlete's feet) as exhibited by an irritating, itchy rash and oozing between her toes, soaks her feet in a 5% peptide (SEQ ID NO: 5) formulation for 10 minutes before bedtime and applies topical 1% peptide formulation twice a day on the infected area and the rest of her feet. The cream formulation is composed of the excipients cetyl alcohol, isopropyl myristate, stearyl alcohol, butylated hydrosyxtoluene, polyoxyethylene stearyl ether, polyoxyethylene stearyl ether, edetate disodium, and purified water. At week 1, the itchiness reduces and the oozing stops. By week 4, the crusty patches of skin are gone and there is no evidence of abnormal skin on her feet. She continues to use 0.05% peptide formulation for 5 years with no further breakout or adverse event.

Example 1.3

A 78 year-old male is diagnosed with onychomycosis after laboratory confirmation of fungal invasion based on microscopic examination and culture of nail scrapings or clippings. He starts painting his finger nails and surrounding nail-bed with 5% peptide (SEQ ID NO:5) formulation twice a day. The cream formulation is composed of the excipients cetyl alcohol, isopropyl myristate, stearyl alcohol, butylated hydroxytoluene, polyoxyethylene stearyl ether, polyoxyethylene stearyl ether, edetate disodium, and purified water. Twelve weeks later, the finger nails that grow in all have normal texture and color. He uses the peptide formulation for 2 years and his nails are all free of fungal infection.

Example 1.4

A 65 year-old male is diagnosed with onychomycosis after laboratory confirmation of fungal invasion based on microscopic examination and culture of nail scrapings or clippings. He starts with oral therapy for 1 month. Afterward, he starts to paint his fingers nails and surrounding nail-bed with 10% peptide (SEQ ID NO: 5) formulation daily. The cream formulation is composed of the excipients cetyl alcohol, isopropyl myristate, stearyl alcohol, butylated hydrosyxtoluenc, polyoxyethylene stearyl ether, polyoxyethylene stearyl ether, edetate disodium, and purified water. Twelve weeks later, the finger nails that grow in all have normal texture and color. He continues using peptide formulation for 2 years and his nails are all free of fungi infection and there is no relapse of additional fungal infection in his toe nails.

Example 1.5

A 10 year-old boy who had has a two-year history of dental caries uses peptide (SEQ ID NO:5) mouth wash for two weeks. The formulation consists of normal saline and 1-5% peptide. His symptoms are significantly relieved. He continues using the peptide mouth wash for two years with no new tooth-cavity observed.

Example 1.6

A 36 year-old woman who has a cold sore outbreak in her mouth applies a 1% peptide (SEQ ID NO: 5) formulation three times a day. The hydrogel formulation is composed of 30% poloxamer. All core sores disappear within two days.

Example 1.7

A 24-year-old women who has genital herpes applies 1% peptide (SEQ ID NO:5) twice a day for a week to the affected area. The cream formulation is composed of the excipients cetyl alcohol, isopropyl myristate, stearyl alcohol, butylated hydroxytoluene, polyoxyethylene stearyl ether, polyoxyethylene stearyl ether, edetate disodium, and purified water. All symptoms disappear at the end of the treatment period.

Example 1.8

An 18-year-old female with a three-year history of rhinitis uses nasal spray containing the peptide of the invention (SEQ ID NO:5) three times a day for a week. The formulation consists of normal saline and 1-5% peptide. She feels immediate relief of symptoms such as itching, sneezing, and nasal congestion.

Example 1.9

A 8 year-old boy who has pink eye, applies the peptide (SEQ ID NO:5) formulation consisting of normal saline and 1-5% peptide, and two days later, the symptoms disappear.

Example 2

In Vitro Antimicrobial Activity

The antimicrobial activity was tested using an exemplary peptide of the invention in a panel of gram-negative and gram-positive bacteria, and fungus. The exemplary peptide sequence was Arg-Lys-Lys-Arg-Arg-Gln-Arg-Arg-Arg-Gly-(Lys)$_{15}$-Gly-Arg-Lys-Lys-Arg-Arg-Gln-Arg-Arg-Arg (SEQ ID NO:5) and it had been formulated in 15% Poloxamer 0.9% saline. The peptide concentrations were 3.3 mg/ml, 11 µg/ml, and 11 ng/ml, respectively. The antimicrobial activities are shown in Tables 1-3. The peptide demonstrated strong antimicrobial activity in a dose-dependent manner. Notably, *Pseudomonas aeruginosa*, a gram-negative bacterium that is noted for its resistance to antibiotics, can be inhibited with 0.33% peptide of the invention (Table 1).

TABLE 1

Anti-microbial Activity at 3.3 mg/ml (0.33% peptide)

| Organism | Initial Count | 14 Days (CFU/ml) | 28 Days (CFU/ml) |
|---|---|---|---|
| *Staphylococcus aureus* ATCC 6538 | $7.4 \times 10^5$ | 125<br>3.8 log reduction | <10<br>No increase |
| *Pseudomonas aeruginosa* ATCC 9027 | $1.1 \times 10^6$ | <100<br>>4.0 log reduction | <100<br>No increase |
| *Escherichia coli* ATCC 8739 | $5.5 \times 10^5$ | <10<br>>4.7 log reduction | <10<br>No increase |
| *Candida albicans* ATCC 10231 | $1.0 \times 10^5$ | <10<br>No increase | <10<br>No increase |
| *Aspergillus niger* ATCC 16404 | $3.0 \times 10^5$ | $3.1 \times 10^5$<br>No increase | $3.0 \times 10^5$<br>No increase |

TABLE 2

Anti-microbial Activity at 11 µg/ml (0.0011% peptide)

| Organism | Initial Count | 14 Days (CFU/ml) | 28 Days (CFU/ml) |
|---|---|---|---|
| *Staphylococcus aureus* ATCC 6538 | $7.0 \times 10^5$ | <10<br>>4.8 log reduction | <10<br>No increase |
| *Pseudomonas aeruginosa* ATCC 9027 | $1.2 \times 10^6$ | $4.3 \times 10^6$<br>0.6 log increase | $1.7 \times 10^7$<br>0.6 log increase |
| *Escherichia coli* ATCC 8739 | $6.9 \times 10^5$ | $1.7 \times 10^3$<br>2.6 log reduction | <10<br>No increase |
| *Candida albicans* ATCC 10231 | $1.6 \times 10^5$ | $2.1 \times 10^3$<br>No increase | $1.0 \times 10^3$<br>No increase |
| *Aspergillus niger* ATCC 16404 | $4.6 \times 10^5$ | $2.5 \times 10^5$<br>No increase | $2.2 \times 10^5$<br>No increase |

TABLE 3

Anti-microbial Activity at 11 ng/ml (0.0000011% peptide)

| Organism | Initial Count | 14 Days (CFU/ml) | 28 Days (CFU/ml) |
|---|---|---|---|
| *Staphylococcus aureus* ATCC 6538 | $7.0 \times 10^5$ | <10<br>>4.8 log reduction | <10<br>No increase |
| *Pseudomonas aeruginosa* ATCC 9027 | $1.2 \times 10^6$ | $3.9 \times 10^6$<br>0.5 log increase | $5.6 \times 10^6$<br>No increase |
| *Escherichia coli* ATCC 8739 | $6.9 \times 10^5$ | $4.0 \times 10^4$<br>1.2 log reduction | 860<br>No increase |
| *Candida albicans* ATCC 10231 | $1.6 \times 10^5$ | $3.8 \times 10^4$<br>No increase | $3.1 \times 10^4$<br>No increase |
| *Aspergillus niger* ATCC 16404 | $4.6 \times 10^5$ | $2.9 \times 10^5$<br>No increase | $2.6 \times 10^5$<br>No increase |

---

What is claimed is:

1. A pharmaceutical composition comprising a cationic peptide, wherein the cationic peptide comprises an amino acid sequence selected from the group consisting of SEQ ID NO: 3, SEQ ID NO: 4, and SEQ ID NO: 5 and a pharmaceutically or cosmetically acceptable carrier and/or diluent.

2. The composition according to claim 1, wherein the cationic peptide comprises the amino acid sequence of SEQ ID NO: 3.

3. The composition according to claim 1, wherein the cationic peptide comprises the amino acid sequence of SEQ ID NO: 4.

4. The composition according to claim 1, wherein the cationic peptide comprises the amino acid sequence of SEQ ID NO: 5.

5. The composition according to claim 2, wherein the composition is a topical composition.

6. The composition according to claim 3, wherein the composition is a topical composition.

7. The composition according to claim 4, wherein the composition is a topical composition.

8. A kit for administering a composition, the kit comprising the composition according to claim 2 and a dispenser.

9. A kit for administering a composition, the kit comprising
the composition according to claim 3 and
a dispenser.

10. A kit for administering a composition, the kit comprising
the composition according to claim 4 and
a dispenser.

11. A kit for administering a composition, the kit comprising
the composition according to claim 5 and
a dispenser.

12. A kit for administering a composition, the kit comprising
the composition according to claim 6 and
a dispenser.

13. A kit for administering a composition, the kit comprising
the composition according to claim 7 and
a dispenser.

14. The composition according to claim 5, wherein the composition is selected from the group consisting of solid compositions, liquid compositions, solutions, emulsions, microemulsions, suspensions, creams, lotions, gels, powders, and nasal sprays.

15. The composition according to claim 14, wherein the composition is a solution.

16. The composition according to claim 14, wherein the composition is a cream.

17. The composition according to claim 14, wherein the composition is a lotion.

18. The composition according to claim 14, wherein the composition is a gel.

19. The composition according to claim 14, wherein the composition is a nasal spray.

20. The composition according to claim 6, wherein the composition is selected from the group consisting of solid compositions, liquid compositions, solutions, emulsions, microemulsions, suspensions, creams, lotions, gels, powders, and nasal sprays.

21. The composition according to claim 20, wherein the composition is a solution.

22. The composition according to claim 20, wherein the composition is a cream.

23. The composition according to claim 20, wherein the composition is a lotion.

24. The composition according to claim 20, wherein the composition is a gel.

25. The composition according to claim 20, wherein the composition is a nasal spray.

26. The composition according to claim 7, wherein the composition is selected from the group consisting of solid compositions, liquid compositions, solutions, emulsions, microemulsions, suspensions, creams, lotions, gels, powders, and nasal sprays.

27. The composition according to claim 26, wherein the composition is a solution.

28. The composition according to claim 26, wherein the composition is a cream.

29. The composition according to claim 26, wherein the composition is a lotion.

30. The composition according to claim 26, wherein the composition is a gel.

31. The composition according to claim 26, wherein the composition is a nasal spray.

32. The composition according to claim 2, wherein the composition contains from about 0.01% w/v to about 20% w/v cationic peptide.

33. The composition according to claim 3, wherein the composition contains from about 0.01% w/v to about 20% w/v cationic peptide.

34. The composition according to claim 4, wherein the composition contains from about 0.01% w/v to about 20% w/v cationic peptide.

35. The composition according to claim 5, wherein the composition contains from about 0.01% w/v to about 20% w/v cationic peptide.

36. The composition according to claim 6, wherein the composition contains from about 0.01% w/v to about 20% w/v cationic peptide.

37. The composition according to claim 7, wherein the composition contains from about 0.01% w/v to about 20% w/v cationic peptide.

38. The kit according to claim 8, further comprising a component to facilitate application of the composition.

39. The kit according to claim 38, wherein said component to facilitate application is selected from the group consisting of a brush, a sponge, and a cotton swab.

40. The kit according to claim 9, further comprising a component to facilitate application of the composition.

41. The kit according to claim 40, wherein said component to facilitate application is selected from the group consisting of a brush, a sponge, and a cotton swab.

42. The kit according to claim 10, further comprising a component to facilitate application of the composition.

43. The kit according to claim 42, wherein said component to facilitate application is selected from the group consisting of a brush, a sponge, and a cotton swab.

44. The kit according to claim 11, further comprising a component to facilitate application of the composition.

45. The kit according to claim 44, wherein said component to facilitate application is selected from the group consisting of a brush, a sponge, and a cotton swab.

46. The kit according to claim 12, further comprising a component to facilitate application of the composition.

47. The kit according to claim 46, wherein said component to facilitate application is selected from the group consisting of a brush, a sponge, or a cotton swab.

48. The kit according to claim 13, further comprising a component to facilitate application of the composition.

49. The kit according to claim 48, wherein said component to facilitate application is selected from the group consisting of a brush, a sponge, or a cotton swab.

50. A cationic peptide comprising the amino acid sequence of SEQ ID NO: 3.

51. The cationic peptide according to claim 50, wherein said peptide consists of the amino acid sequence of SEQ ID NO: 3.

52. A cationic peptide comprising the amino acid sequence of SEQ ID NO: 4.

53. The cationic peptide according to claim 52, wherein said peptide consists of the amino acid sequence of SEQ ID NO: 4.

54. A cationic peptide comprising the amino acid sequence of SEQ ID NO: 5.

55. The cationic peptide according to claim 54, wherein said peptide consists of the amino acid sequence of SEQ ID NO: 5.

* * * * *

SEQUENCE LISTING

<160> NUMBER OF SEQ ID NOS: 5

<210> SEQ ID NO 1
<211> LENGTH: 9
<212> TYPE: PRT
<213> ORGANISM: Human immunodeficiency virus

<400> SEQUENCE: 1

Arg Lys Lys Arg Arg Gln Arg Arg Arg
1               5

<210> SEQ ID NO 2
<211> LENGTH: 9
<212> TYPE: PRT
<213> ORGANISM: Artificial Sequence
<220> FEATURE:
<223> OTHER INFORMATION: HIV TAT antimicrobial peptide

<400> SEQUENCE: 2

Arg Arg Arg Gln Arg Arg Lys Lys Arg
1               5

```
<210> SEQ ID NO 3
<211> LENGTH: 40
<212> TYPE: PRT
<213> ORGANISM: Artificial Sequence
<220> FEATURE:
<223> OTHER INFORMATION: HIV TAT antimicrobial peptide
<220> FEATURE:
<221> NAME/KEY: MISC_FEATURE
<222> LOCATION: (16)..(30)
<223> OTHER INFORMATION: Lys is optional

<400> SEQUENCE: 3

Arg Lys Lys Arg Arg Gln Arg Arg Arg Gly Lys Lys Lys Lys Lys
1               5                   10                  15

Lys Lys Lys Lys Lys Lys Lys Lys Lys Lys Lys Lys Lys Gly Arg
            20                  25                  30

Lys Lys Arg Arg Gln Arg Arg Arg
        35                  40

<210> SEQ ID NO 4
<211> LENGTH: 40
<212> TYPE: PRT
<213> ORGANISM: Artificial Sequence
<220> FEATURE:
<223> OTHER INFORMATION: HIV TAT antimicrobial peptide
<220> FEATURE:
<221> NAME/KEY: MISC_FEATURE
<222> LOCATION: (16)..(30)
<223> OTHER INFORMATION: Lys is optional

<400> SEQUENCE: 4

Arg Arg Arg Gln Arg Arg Lys Lys Arg Gly Lys Lys Lys Lys Lys
1               5                   10                  15

Lys Lys Lys Lys Lys Lys Lys Lys Lys Lys Lys Lys Lys Gly Arg
            20                  25                  30

Arg Arg Gln Arg Arg Lys Lys Arg
        35                  40

<210> SEQ ID NO 5
<211> LENGTH: 35
<212> TYPE: PRT
<213> ORGANISM: Artificial Sequence
<220> FEATURE:
<223> OTHER INFORMATION: HIV TAT antimicrobial peptide

<400> SEQUENCE: 5

Arg Lys Lys Arg Arg Gln Arg Arg Arg Gly Lys Lys Lys Lys Lys
1               5                   10                  15

Lys Lys Lys Lys Lys Lys Lys Lys Gly Arg Lys Lys Arg Arg Gln
            20                  25                  30

Arg Arg Arg
        35
```